United States Patent
Wright et al.

(10) Patent No.: US 10,441,321 B2
(45) Date of Patent: Oct. 15, 2019

(54) RIB HOOK DEVICES, SYSTEMS, AND METHODS OF USE

(71) Applicants: MUSC Foundation for Research Development, Charleston, SC (US); Clemson University Research Foundation, Clemson, SC (US)

(72) Inventors: Gregory J. Wright, Charleston, SC (US); Hai Yao, Mt. Pleasant, SC (US); Richard H. Gross, Mt. Pleasant, SC (US)

(73) Assignees: CLEMSON UNIVERSITY RESEARCH FOUNDATION, Clemson, SC (US); MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 62 days.

(21) Appl. No.: 15/374,615

(22) Filed: Dec. 9, 2016

(65) Prior Publication Data
US 2017/0164984 A1 Jun. 15, 2017

Related U.S. Application Data

(60) Provisional application No. 62/266,493, filed on Dec. 11, 2015.

(51) Int. Cl.
*A61B 17/70* (2006.01)

(52) U.S. Cl.
CPC ........ *A61B 17/7056* (2013.01); *A61B 17/707* (2013.01)

(58) Field of Classification Search
CPC .......................... A61B 17/7056; A61B 17/707
See application file for complete search history.

(56) References Cited

U.S. PATENT DOCUMENTS

| | | |
|---|---|---|
| 5,800,434 A | 9/1998 | Campbell, Jr. |
| 8,236,002 B2 | 8/2012 | Fortin et al. |
| 8,241,334 B2 | 8/2012 | Butler et al. |
| 2008/0306538 A1 | 12/2008 | Moore et al. |
| 2010/0331844 A1* | 12/2010 | Ellis .................... A61B 17/8076 606/70 |
| 2011/0184463 A1 | 7/2011 | Schwend |
| 2014/0222074 A1* | 8/2014 | Rathbun ............ A61B 17/7014 606/258 |

FOREIGN PATENT DOCUMENTS

| | | | | |
|---|---|---|---|---|
| FR | 2642642 A1 * | 8/1990 | ......... | A61B 17/7056 |
| FR | 2642642 A1 * | 8/1990 | ......... | A61B 17/7056 |

OTHER PUBLICATIONS

Translation of FR 2642642, provided by EPO, accessed on Aug. 16, 2018.*

* cited by examiner

*Primary Examiner* — Julianna N Harvey
(74) *Attorney, Agent, or Firm* — Heslin Rothenberg Farley & Mesiti P.C.; Jacquelyn A. Graff, Esq.

(57) ABSTRACT

Rib hook devices, systems, and methods of assembling and using the devices and systems are disclosed. The rib hook device includes a body with a first end and a second end and a rod attachment member coupled to and extending away from the second end of the body. The rib hook system includes at least one rib hook device, a first rod for engaging the at least one rib hook device, and at least one fastener for securing the first rod to the at least one rib hook device. Methods for assembling and using the rib hook devices and systems are also disclosed.

20 Claims, 23 Drawing Sheets

RIB HOOK DEVICES, SYSTEMS, AND METHODS OF USE

CROSS REFERENCE TO RELATED APPLICATION

This application claims priority benefit under 35 U.S.C. § 119(e) of U.S. provisional patent application No. 62/266,493 filed Dec. 11, 2015, which is incorporated herein by reference in its entirety.

FIELD OF THE INVENTION

The present invention relates generally to a medical implant for correction of spinal deformities. More specifically, but not exclusively, the present invention concerns rib hook devices for coupling to a patient's ribs to correct spinal deformities in patients.

BACKGROUND OF THE INVENTION

Scoliosis, osteoporosis, kyphosis, and other diseases or trauma may cause deformities to a patient's spine. The currently used methods of correction include distal fixation that is anchored to the lower lumbar by sacral S-hooks or pedicle screws and upper thoracic fixation anchored using pedicle screws or lamina hooks. For scoliosis a thoracic technique may be used which includes use of a growing rod that is fixed to a patient's spine with pedicle screws. A common complication from the currently used fixation methods occurs at the points of fixation and may include either pedicle screw pullout or lamina hook failure. Thus, improved implants and methods of correction are needed to prevent these failures.

SUMMARY OF THE INVENTION

Aspects of the present invention provide rib hook devices and systems for coupling to a patient's ribs to correct spinal deformities in patients due to diseases or trauma and methods of using the same.

In one aspect, provided herein is a rib hook device, including a body with a first end and a second end and a rod attachment member coupled to and extending away from the second end of the body.

In another aspect, provided herein is a rib hook system including at least one rib hook device, a first rod for engaging the at least one rib hook device, and at least one fastener for securing the first rod to the at least one rib hook device.

In yet another aspect, provided herein is a method for using a rib hook system, including obtaining a rib hook system. The rib hook system including at least one rib hook device, a first rod, and at least one fastener. The method may also include exposing at least a portion of a patient's ribs and coupling a first rib hook device of the at least one rib hook device to a first rib. The method may further include coupling a second rib hook device of the at least one rib hook device to a second rib and inserting the first rod to engage the first rib hook device and the second rib hook device. Finally, the method may include securing the first rod to the first rib hook device and the second rib hook device and closing the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
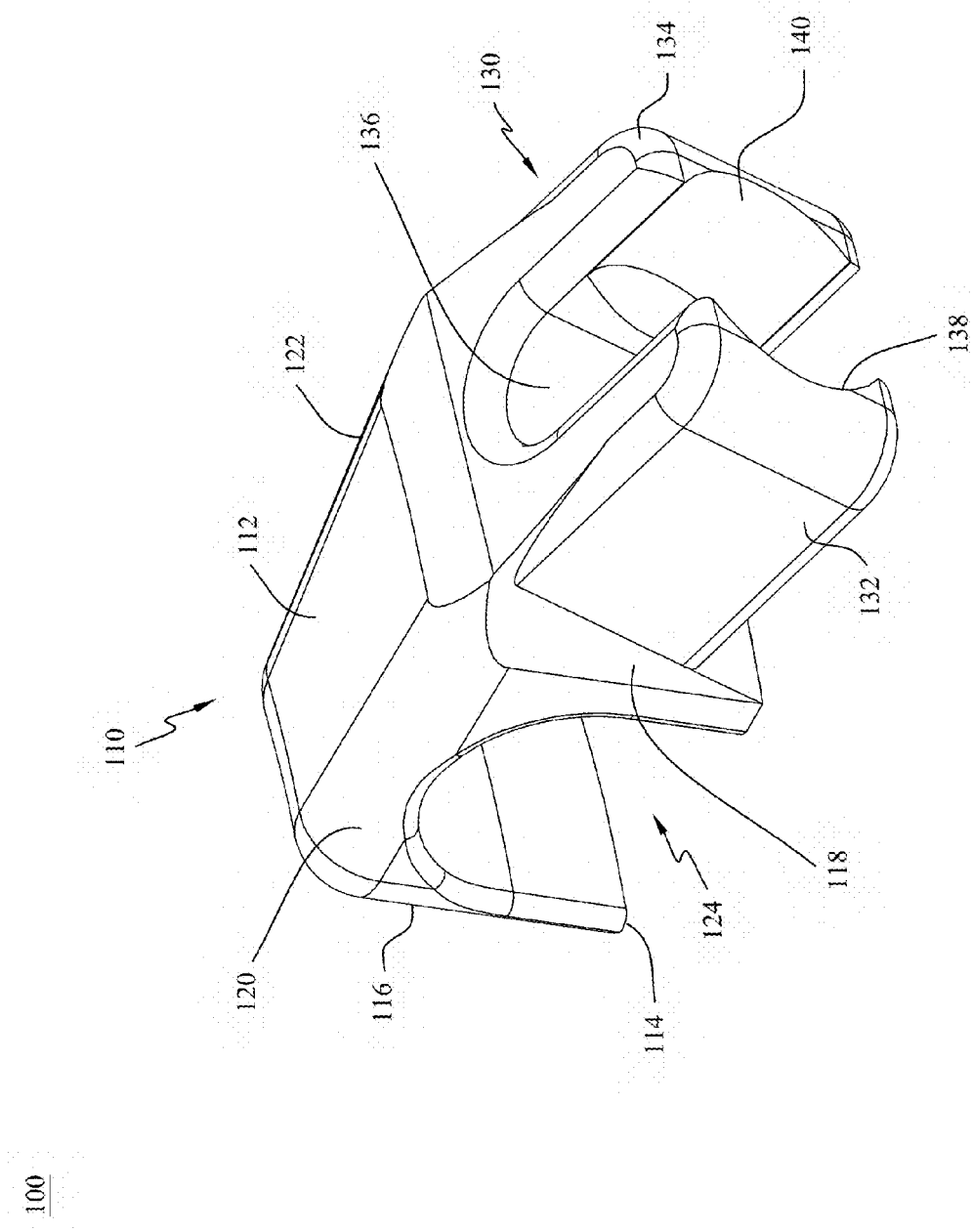
FIG. 1 is a side perspective view of a rib hook device, in accordance with an aspect of the present invention.
Figure 2:
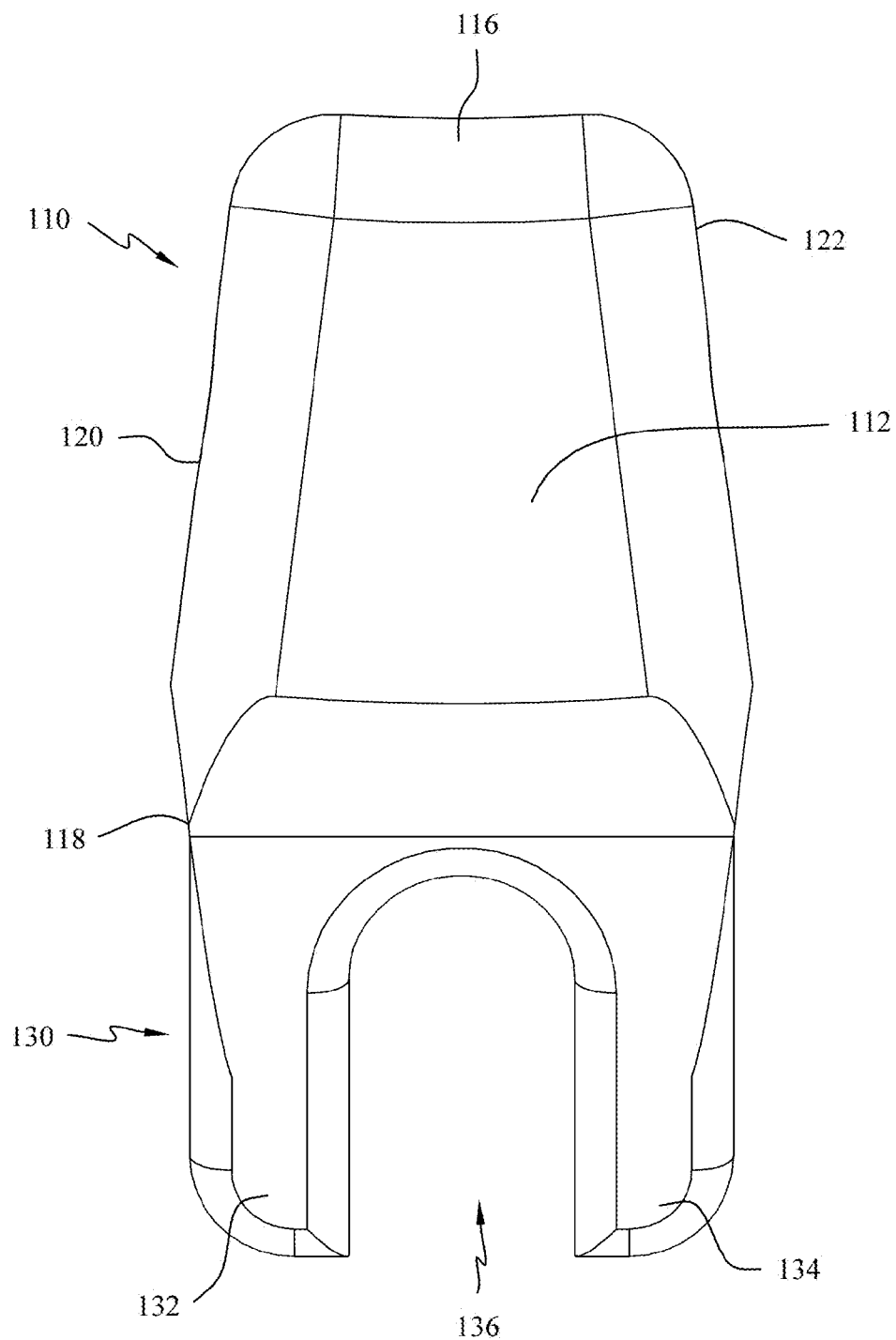
FIG. 2 is a top view of the rib hook device of FIG. 1, in accordance with an aspect of the present invention.
Figure 3:
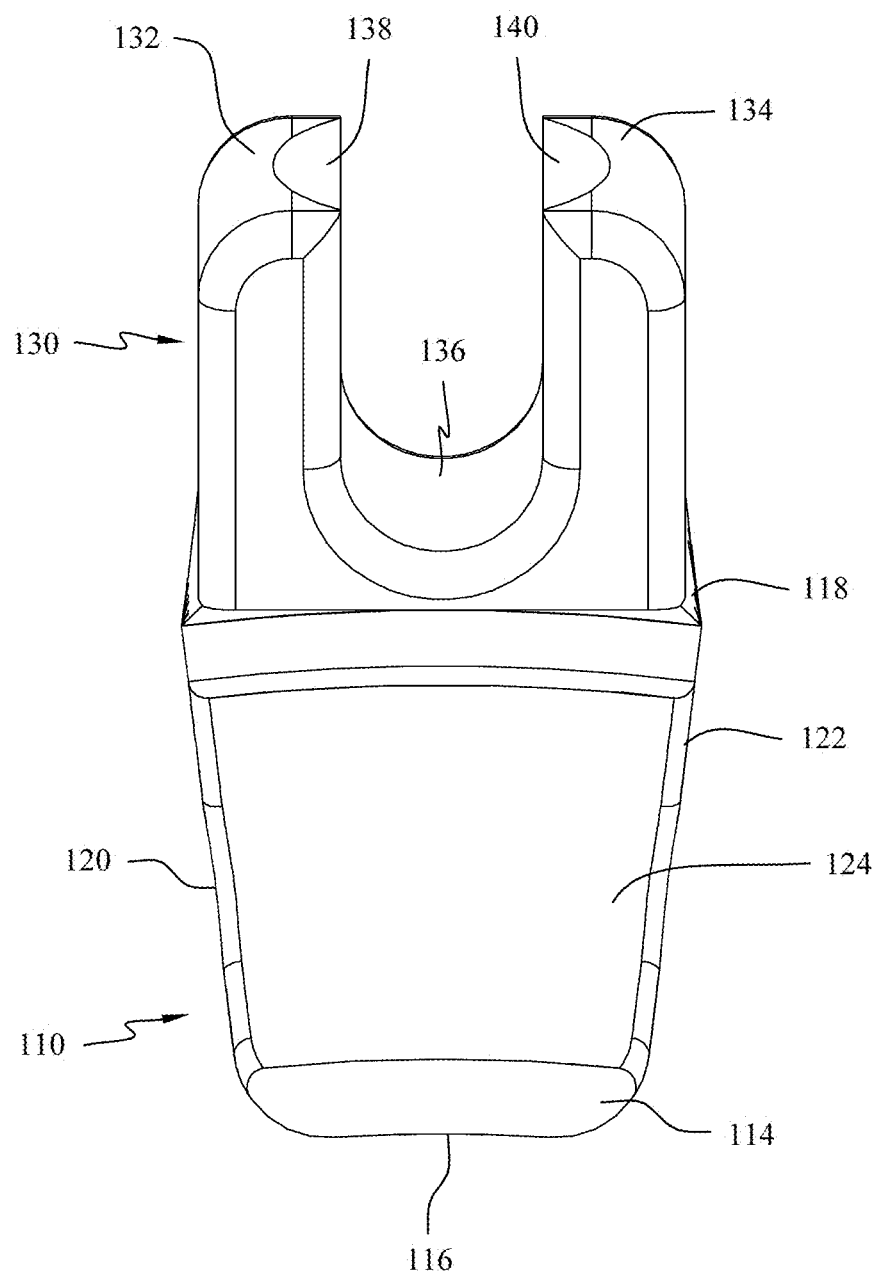
FIG. 3 is a bottom view of the rib hook device of FIG. 1, in accordance with an aspect of the present invention.
Figure 4:
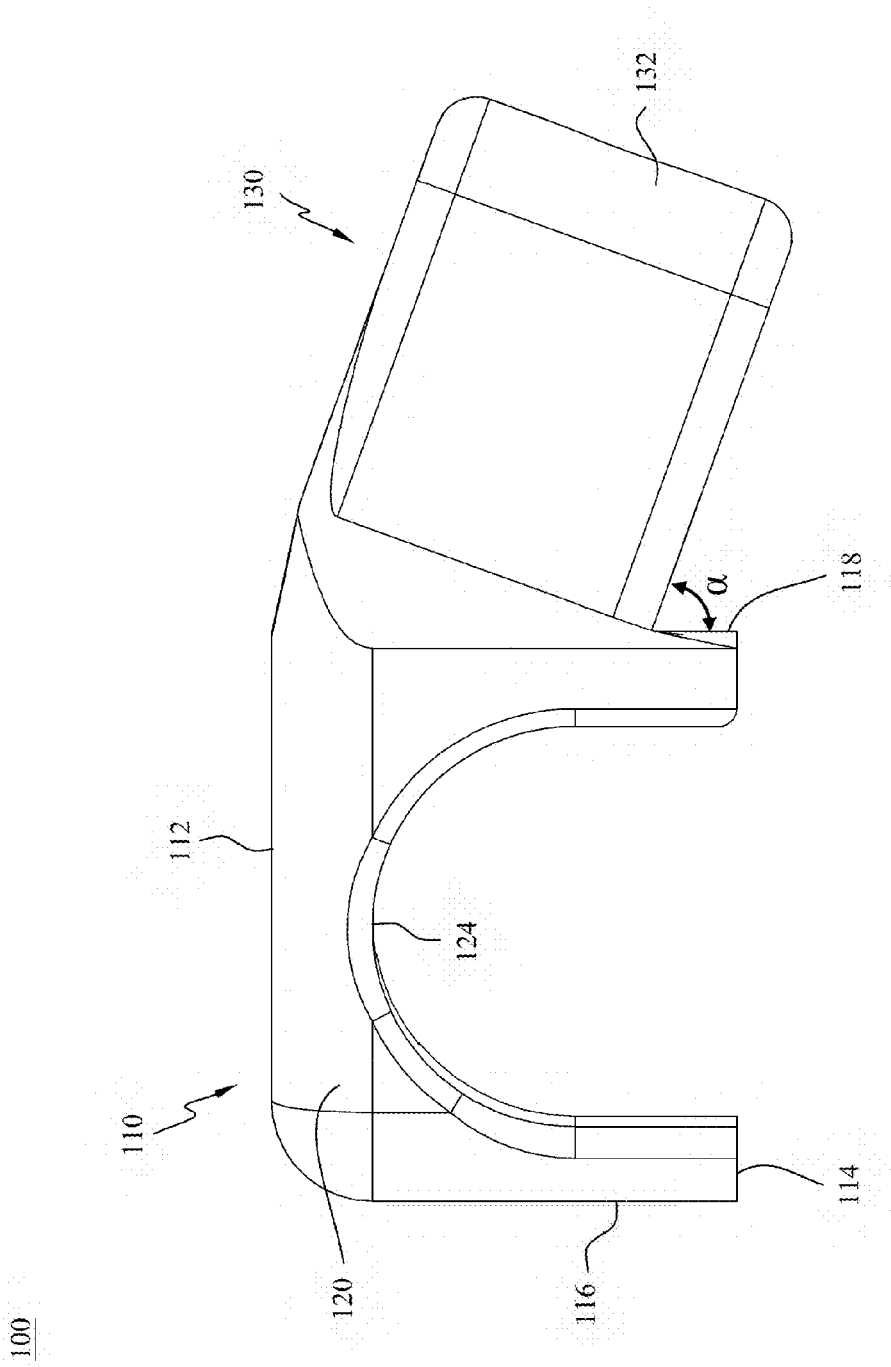
FIG. 4 is a side view of the rib hook device of FIG. 1, in accordance with an aspect of the present invention.
Figure 5:
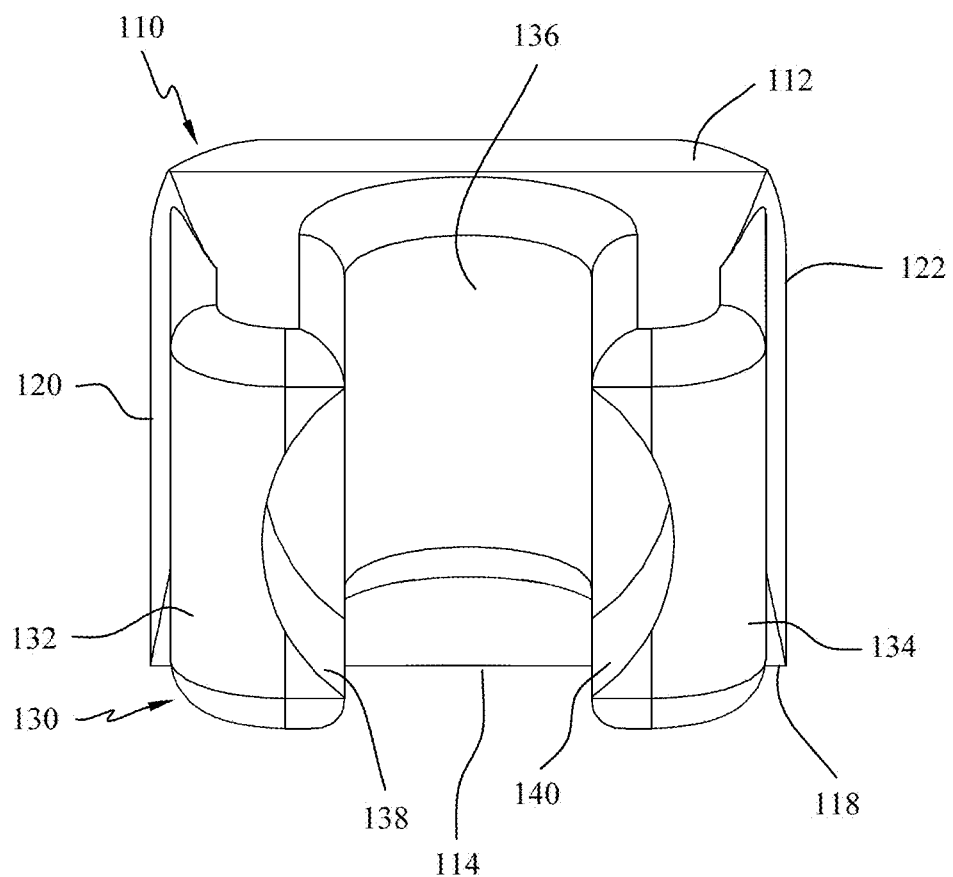
FIG. 5 is a second end view of the rib hook device of FIG. 1, in accordance with an aspect of the present invention.
Figure 6:
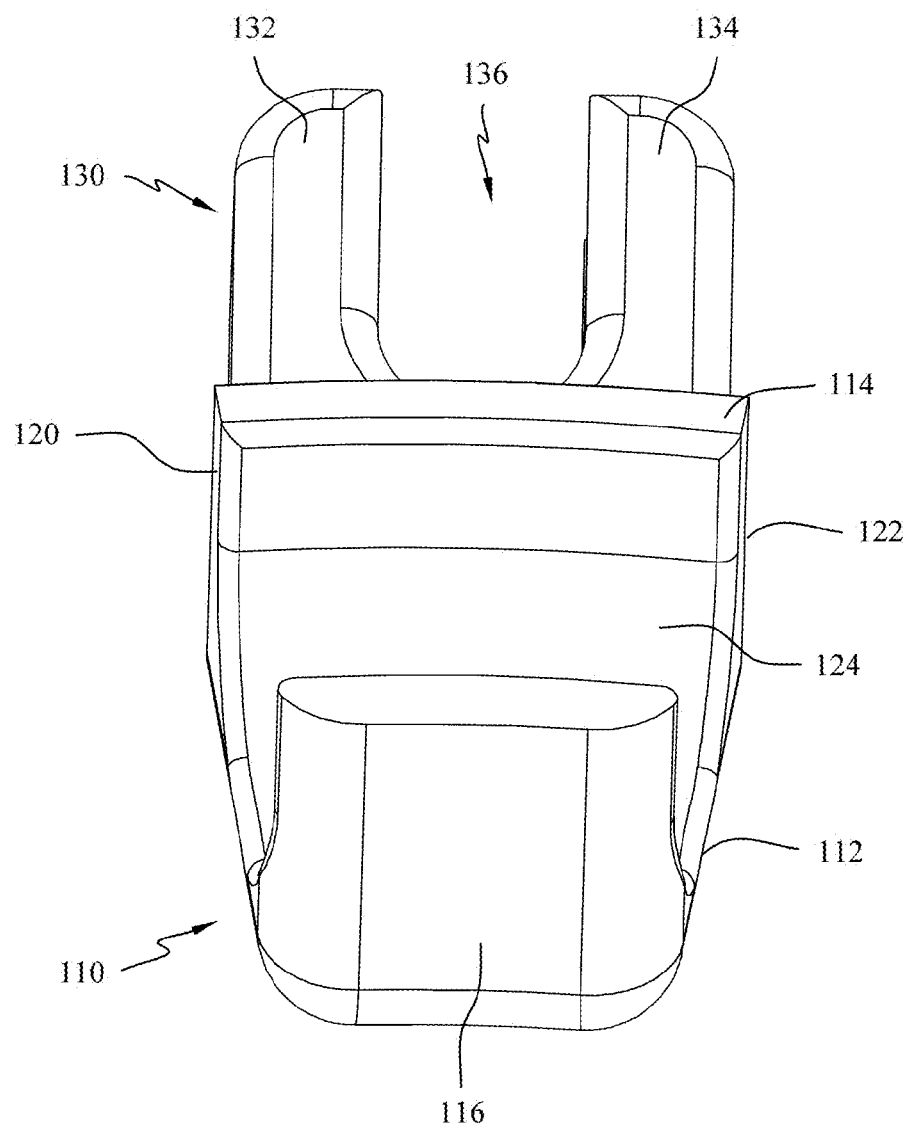
FIG. 6 is a first end, bottom perspective view of the rib hook device of FIG. 1, in accordance with an aspect of the present invention.
Figure 7:
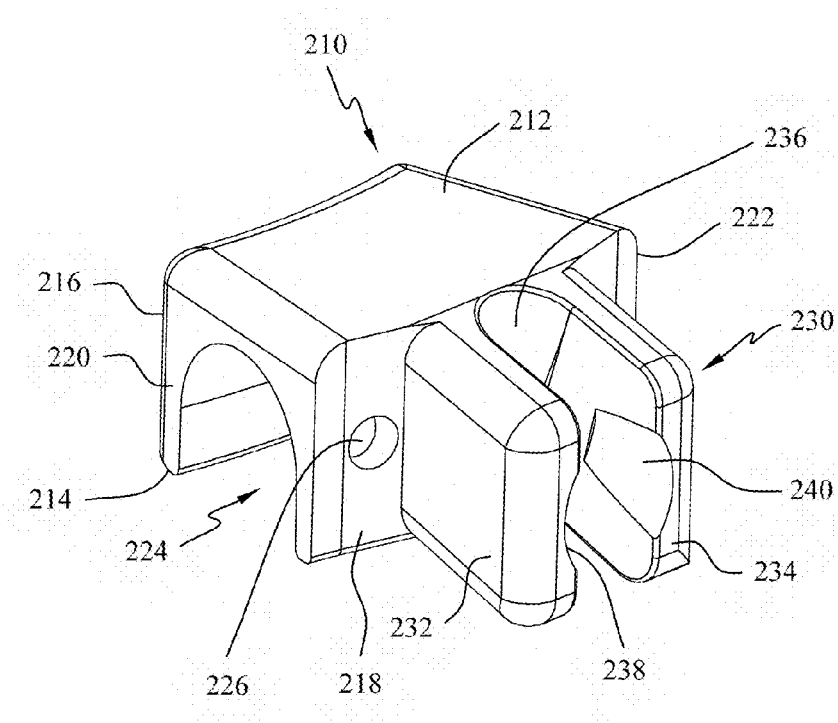
FIG. 7 is a side perspective view of another embodiment rib hook device, in accordance with an aspect of the present invention.
Figure 8:
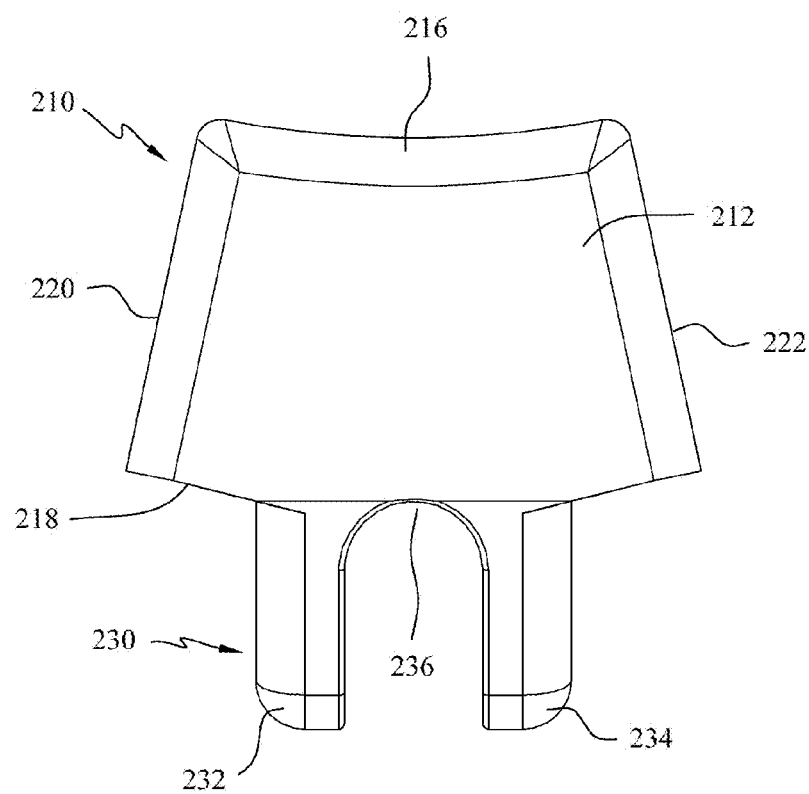
FIG. 8 is a top view of the rib hook device of FIG. 7, in accordance with an aspect of the present invention.

Generally stated, disclosed herein are rib hook devices and systems for coupling to a patient's ribs to correct spinal deformities in patients due to, for example, scoliosis, kyphosis, osteoporosis, or diseases or trauma. Further, methods of assembling and using the rib hook devices and systems are discussed.

In this detailed description and the following claims, the words proximal, distal, anterior, posterior, medial, lateral, superior, inferior, cephalad, caudal, transverse and sagittal are defined by their standard usage for indicating a particular part of a patient's body or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, "inferior" means a direction below another object or structure, "cephalad" means a direction toward the head, and "caudal" means a direction toward the inferior part of the body. The "transverse plane" refers to the plane that divides the body into superior and inferior portions. The "sagittal plane" refers to the plane that divides the body into left and right portions.

Referring to the drawings, wherein like reference numerals are used to indicate like or analogous components throughout the several views, and with particular reference to FIGS. 1-6, there is illustrated an exemplary embodiment of a rib hook device 100. The terms "rib hook device," "hook device," "device," and "implant" may be used interchangeably herein as they essentially describe the same type of device. The rib hook device 100 may include a body 110 and a rod attachment member 130 coupled to the body 110. The body 110 may include a top side 112, a bottom side 114, a first end 116, a second end 118, a first side 120, and a second side 122. The top side 112 may be positioned opposite the bottom side 114. The first end 116 may be positioned opposite the second end 118. The first side 120 may be positioned opposite the second side 122. A channel 124 may extend into the body 110 from the bottom side 114 toward the top side 112. The channel 124 may also extend through the body 110 from the first side 120 to the second side 122. The channel 124 may include a radius in the sagittal plane and the radius may be, for example, sized to correspond to the size of a patient's ribs. The radius of the channel 124 may be, for example, approximately 2.5 millimeters to 10 millimeters to correspond to the thickness of a patient's ribs at the point of contact. The channel 124 may be, for example, arc shaped, as shown in the side view of FIG. 4. The body 110 may have, for example, a curvature with a radius in the transverse plane. The radius of the body 110 may be, for example, between approximately 20 millimeters and 60 millimeters covering both pediatric and adult patients. The radius of the body 110 may be selected, for example, to match the curvature of a patient's rib. The size of the radius and length of the channel 124 of the body 110 may be selected to increase contact area with the patient's rib and distribute the force exerted by the rib hook device 100 over the length of the channel 124.

Figure 22:
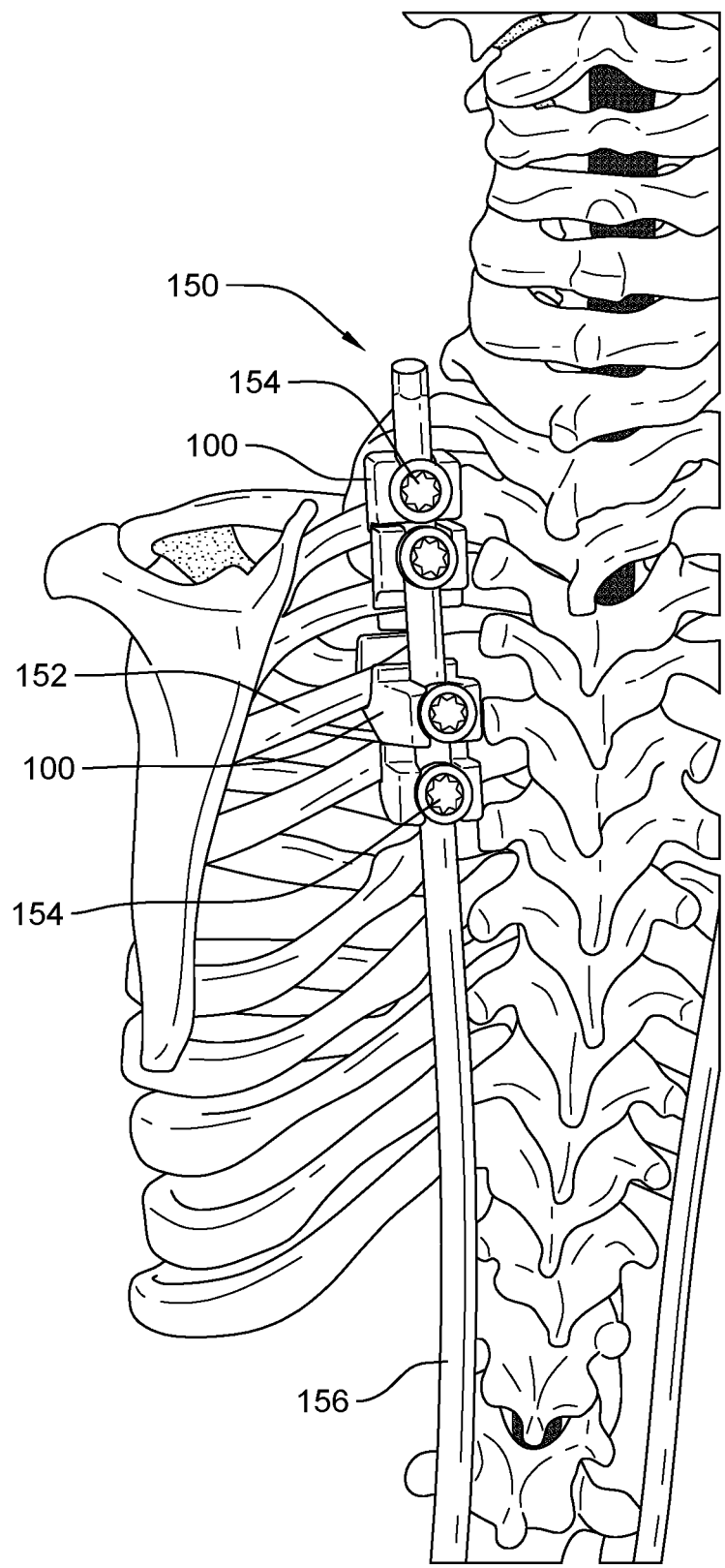
FIG. 22 is a posterior view of a plurality of rib hook devices of FIG. 1 on a patient's ribs, in accordance with an aspect of the present invention.

The rod attachment member 130 may extend out from the second end 118 of the body 110. With specific reference to FIG. 4, the rod attachment member 130 may extend away from the body 110 at an angle α. The angle α may be, for example, a cant angle that may be approximately 5° to 50°. In one embodiment, the angle α may be, for example, 20°. The attachment member 130 may include a first arm 132 and a second arm 134. The first arm 132 and the second arm 134 may be spaced apart to form a groove 136 between the arms 132, 134. The groove 136 may be sized and shaped to receive a rod 156, as shown in FIG. 22. The groove 136 may have, for example, an end that is shaped to match the shape of a rod, such as, a curved, arced, planar or angled shape. The groove 136 may be, for example, arc shaped, as best seen in the top view of FIG. 2. The first arm 132 may include, for example, a recess 138 on the inside of the first arm 132. The second arm 134 may include, for example, a recess 140 on the inside of the second arm 134. The recesses 138, 140 may be, for example, curved to receive fasteners 154, as shown in FIG. 22. The fasteners may be, for example, screws, set screws, and the like to secure the rod 156 in the groove 136.

The rib hook device 100 may be, for example, a pediatric rib hook device sized to fit onto the ribs of a pediatric patient. Referring now to FIG. 22, a rib hook system 150 positioned on a patient's ribs 152 is shown. The rib hook system 150 may include a plurality of rib hook devices 100, a plurality of set screws 154, and a rod 156. At least one first rib hook device 100 of the plurality of rib hook devices 100 may be attached to a first rib 152 with the channel 124 open, for example, in a caudal direction. At least one second rib hook device 100 of the plurality of rib hook devices 100 may be attached to a second rib 152 with the channel 124 open, for example, in a cephalad direction. Although not shown, the at least one first rib hook device 100 and the at least one second rib hook device 100 may be positioned on the ribs in either a caudal or cephalad direction as desired by the surgeon to achieve the desired spinal correction. When the plurality of rib hook devices 100 are positioned on the patient's ribs, the attachment members 130 of each rib hook device 100 may extend out from the ribs in, for example, a generally posterior direction. The rod 156 may then be set into the groove 136 of each of the at least one first rib hook device 100 and the at least one second rib hook device 100 and secured to the rib hook devices 100 with fasteners 154, for example, set screws. The number of at least one first rib hook devices 100 and at least one second rib hook devices 100 may be selected based on the spinal deformity being corrected.

Referring now to FIGS. 7-12, there is illustrated an exemplary embodiment of a rib hook device 200. The terms "rib hook device," "hook device," "device," and "implant" may be used interchangeably herein as they essentially describe the same type of device. The rib hook device 200 may include a body 210 and a rod attachment member 230 coupled to and extending away from the body 210. The body 210 may include a top side 212, a bottom side 214, a first end 216, a second end 218, a first side 220, and a second side 222. The top side 212 may be positioned opposite the bottom side 214. The first end 216 may be positioned opposite the second end 218. The first side 220 may be positioned opposite the second side 222. A channel 224 may extend into the body 210 from the bottom side 214 toward the top side 212. The channel 224 may also extend through the body 210 from the first side 220 to the second side 222. The channel 224 may include a radius in the sagittal plane and the radius may be, for example, sized to correspond to the size of a patient's ribs. The radius of the channel 224 may be, for example, approximately 2.5 millimeters to 10 millimeters to correspond to the thickness of a patient's ribs. The channel 224 may be, for example, arc shaped, as shown in the side view of FIG. 10. The body 210 may also have, for example, a curvature with a radius in the transverse plane. The radius of the body 210 may be, for example, between approximately 20 millimeters and 60 millimeters covering both pediatric and adult patients. The radius of the body 210 may be selected, for example, to match the curvature of a patient's rib. The size of the radius and length of the channel 224 of the body 210 may be selected to increase the contact area with the patient's rib and distribute the force applied to the rib over the length of the channel 224.

Figure 9:
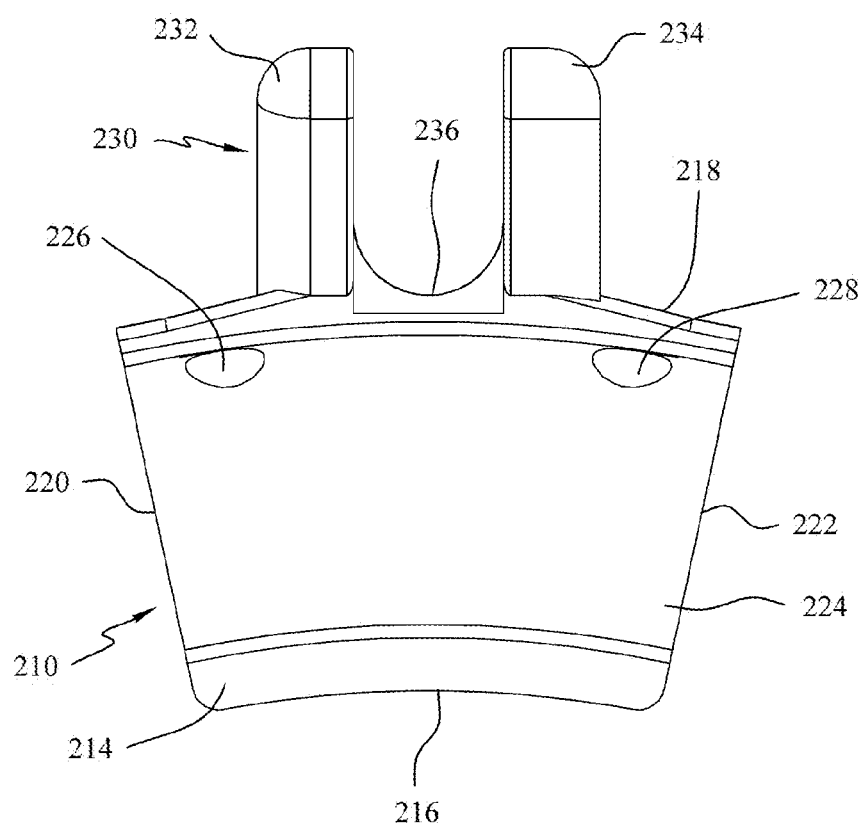
FIG. 9 is a bottom view of the rib hook device of FIG. 7, in accordance with an aspect of the present invention.
Figure 10:
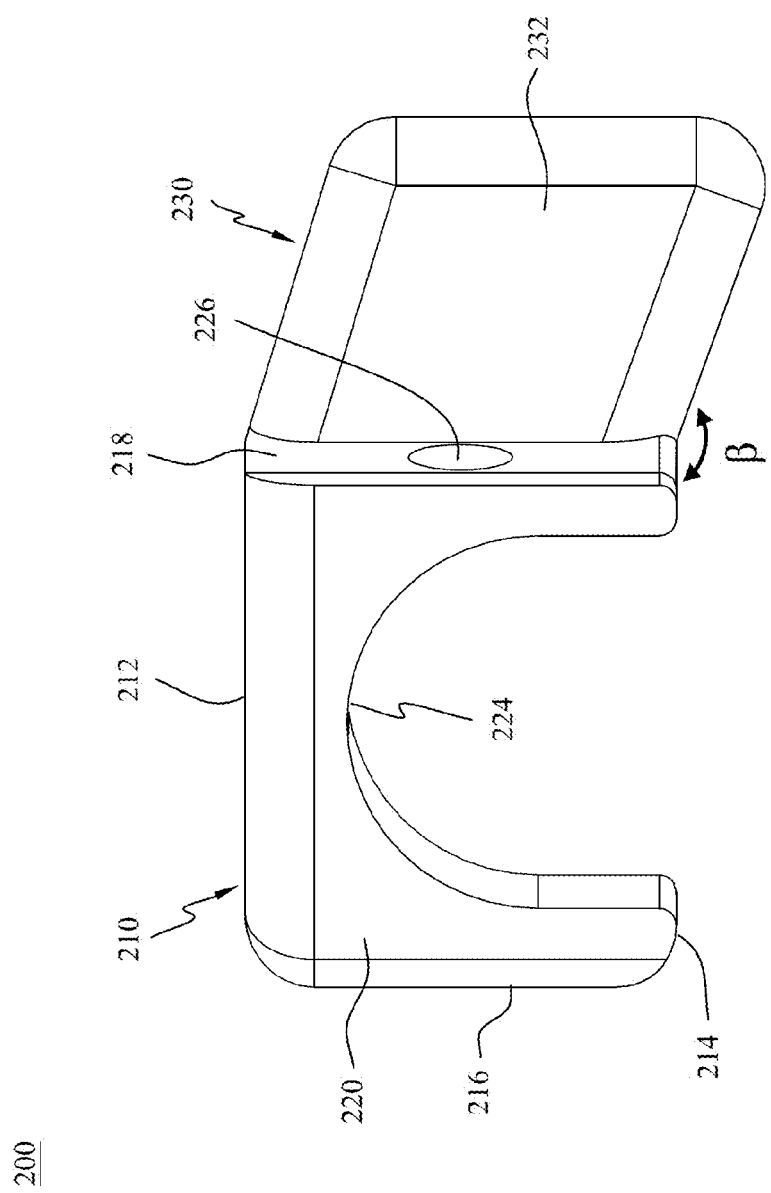
FIG. 10 is a side view of the rib hook device of FIG. 7, in accordance with an aspect of the present invention.
Figure 11:
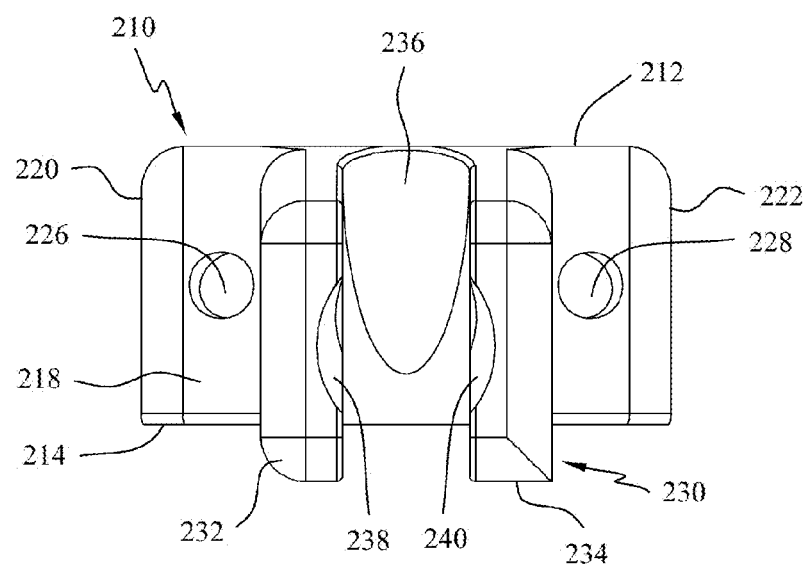
FIG. 11 is a second end view of the rib hook device of FIG. 7, in accordance with an aspect of the present invention.
Figure 12:
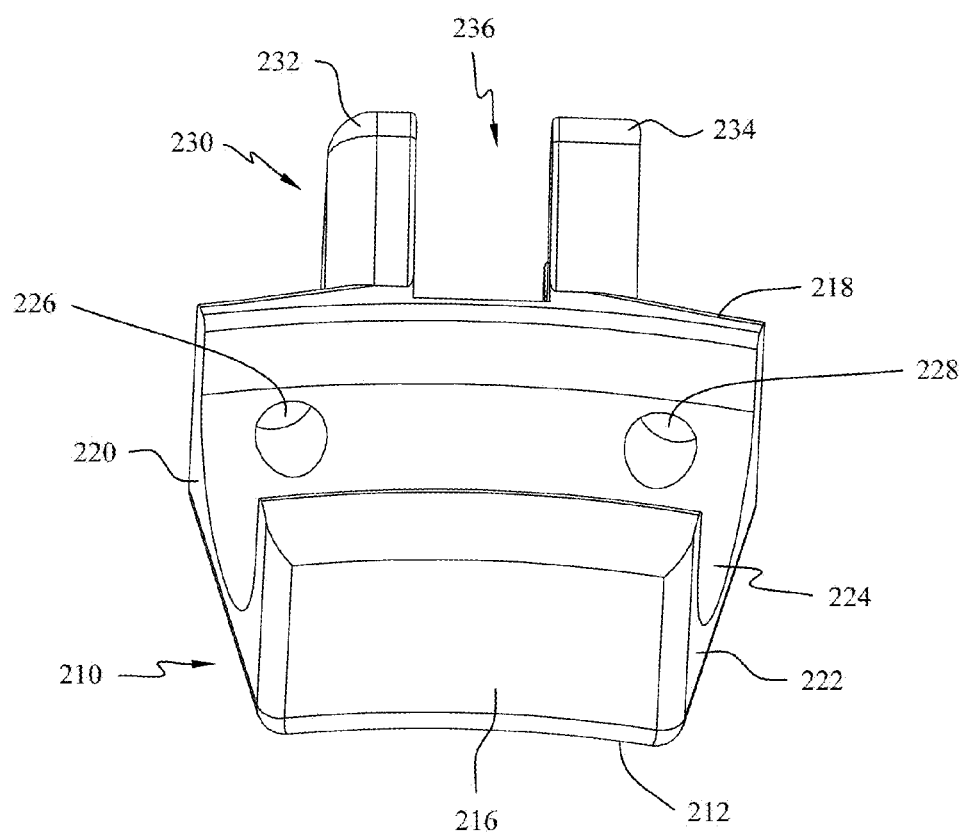
FIG. 12 is a first end, bottom perspective view of the rib hook device of FIG. 7, in accordance with an aspect of the present invention.
Figure 13:
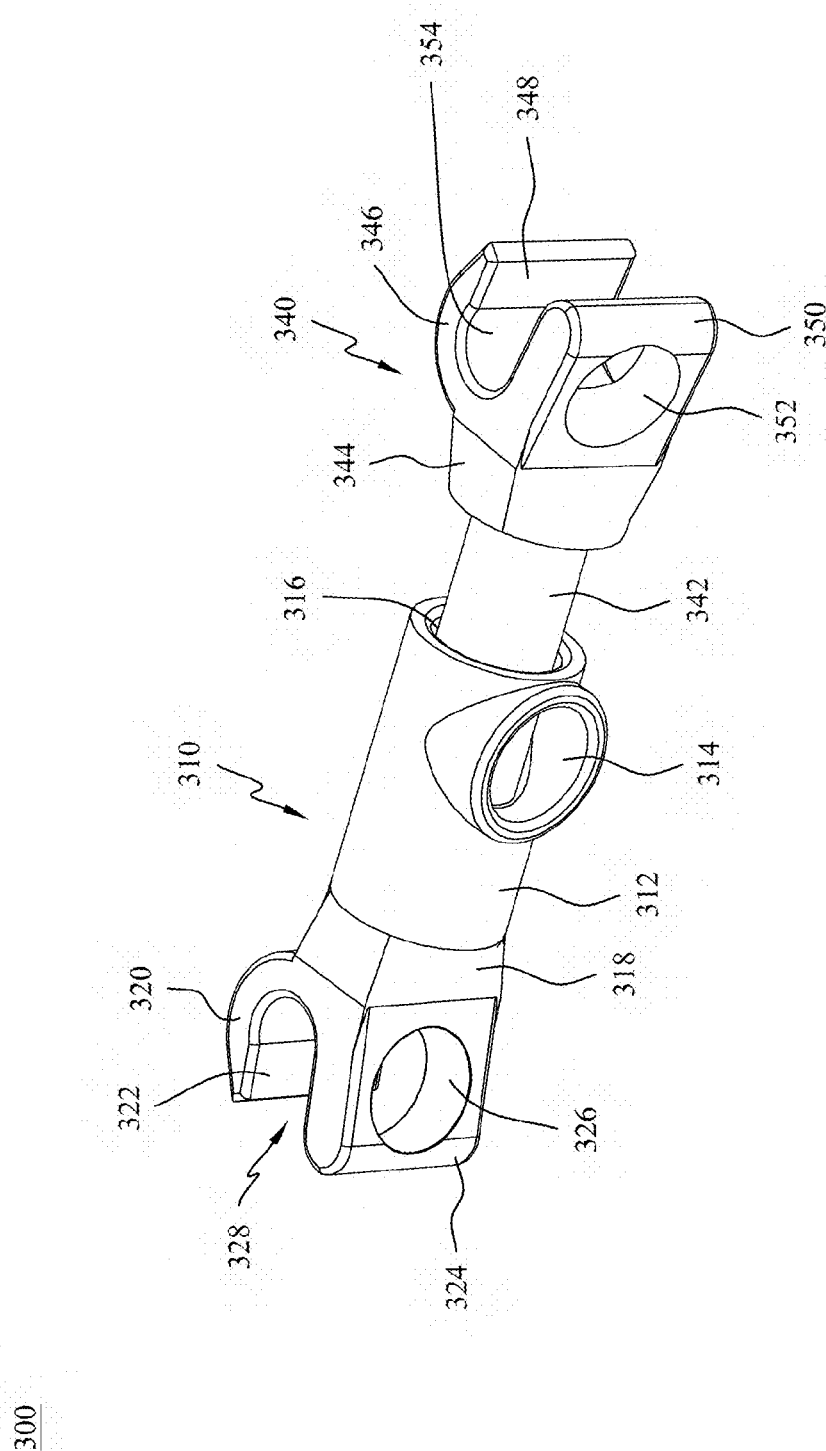
FIG. 13 is a perspective view of a connector member, in accordance with an aspect of the present invention.
Figure 14:
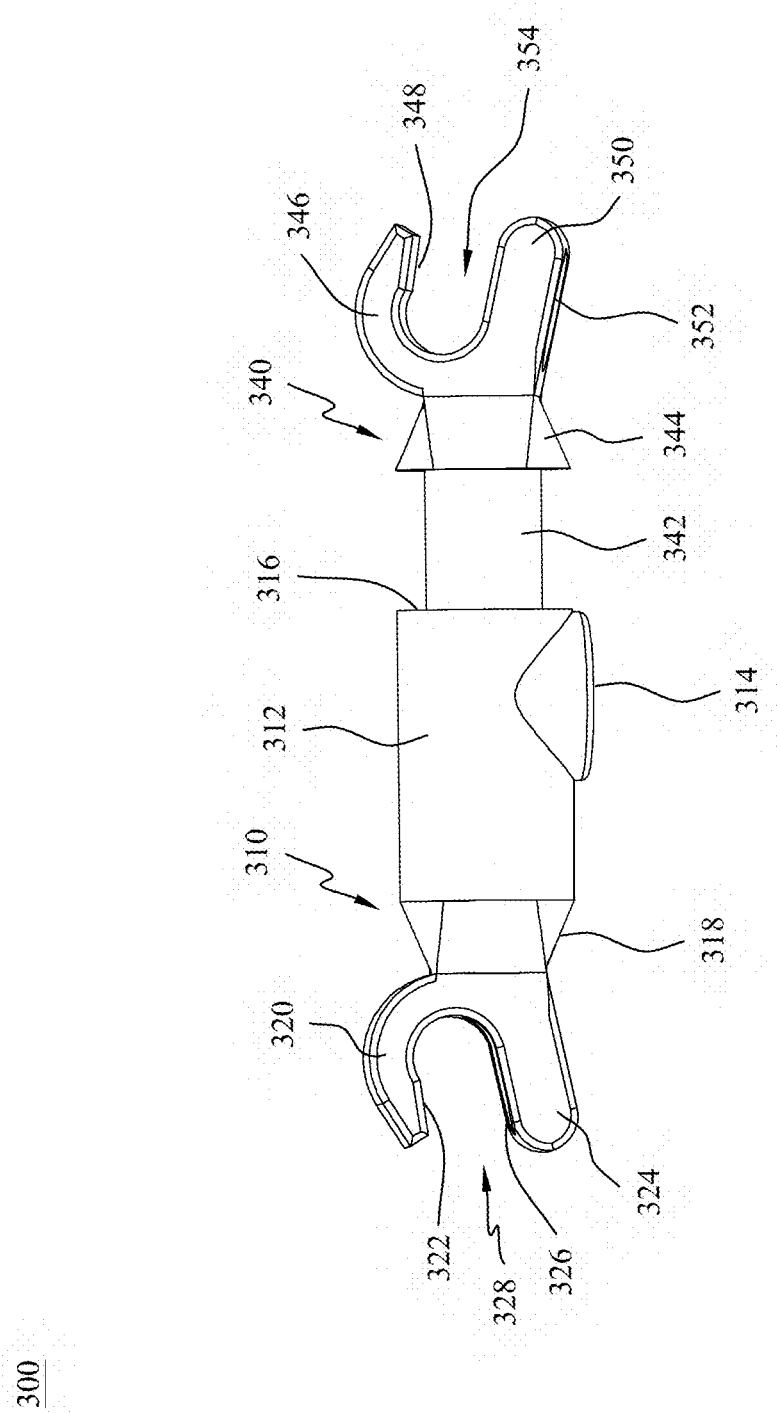
FIG. 14 is a top view of the connector member of FIG. 13, in accordance with an aspect of the present invention.
Figure 15:
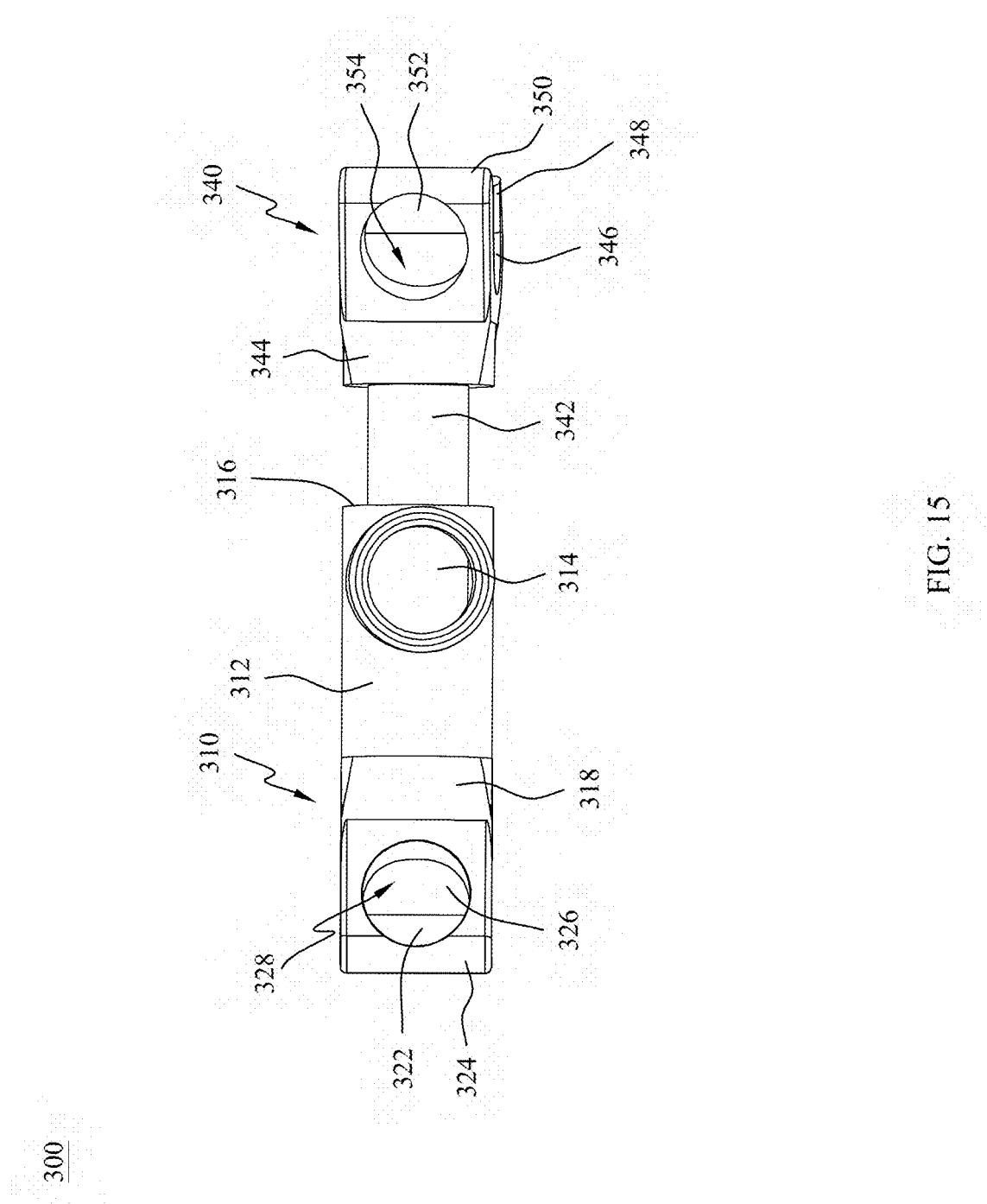
FIG. 15 is a side view of the connector member of FIG. 13, in accordance with an aspect of the present invention.
Figure 16:
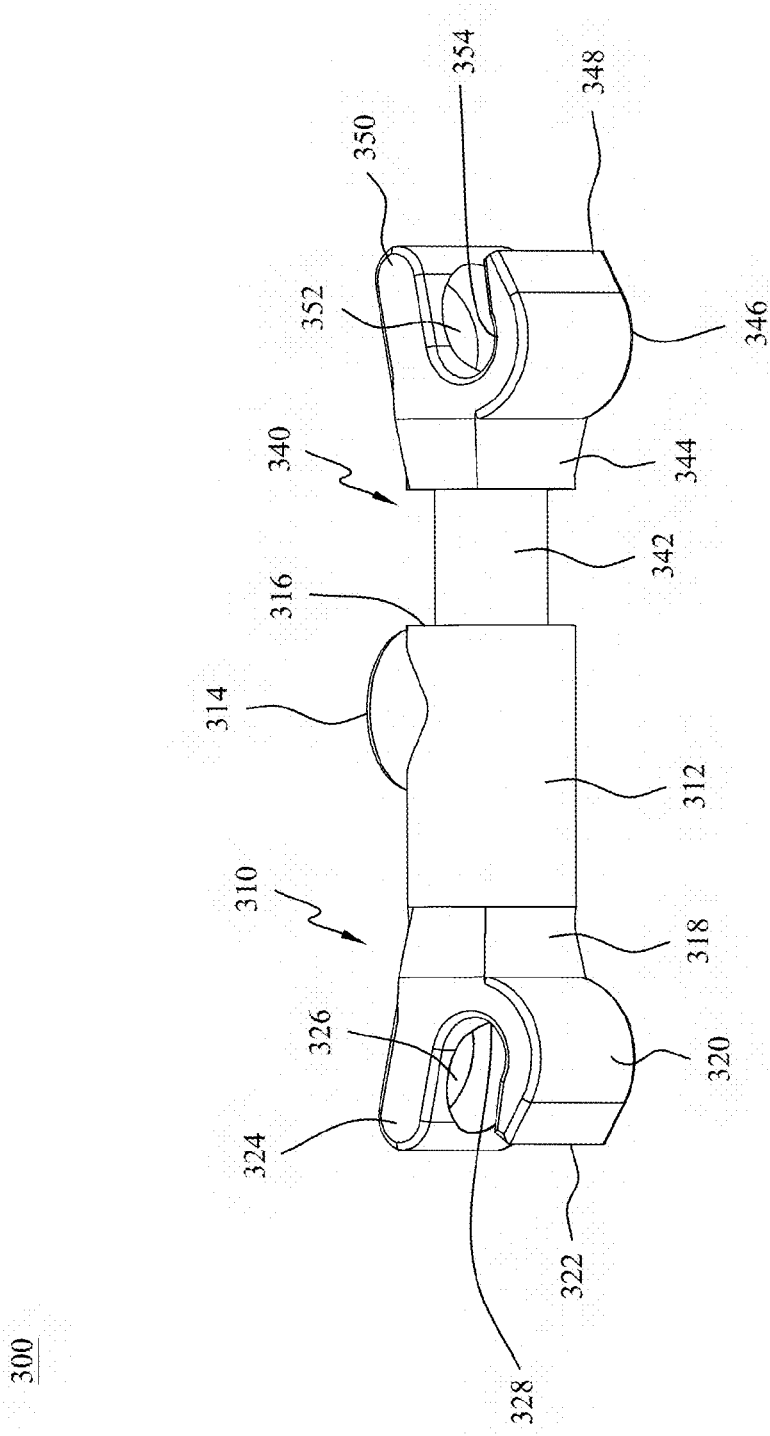
FIG. 16 is a side perspective view of the connector member of FIG. 13, in accordance with an aspect of the present invention.
Figure 17:
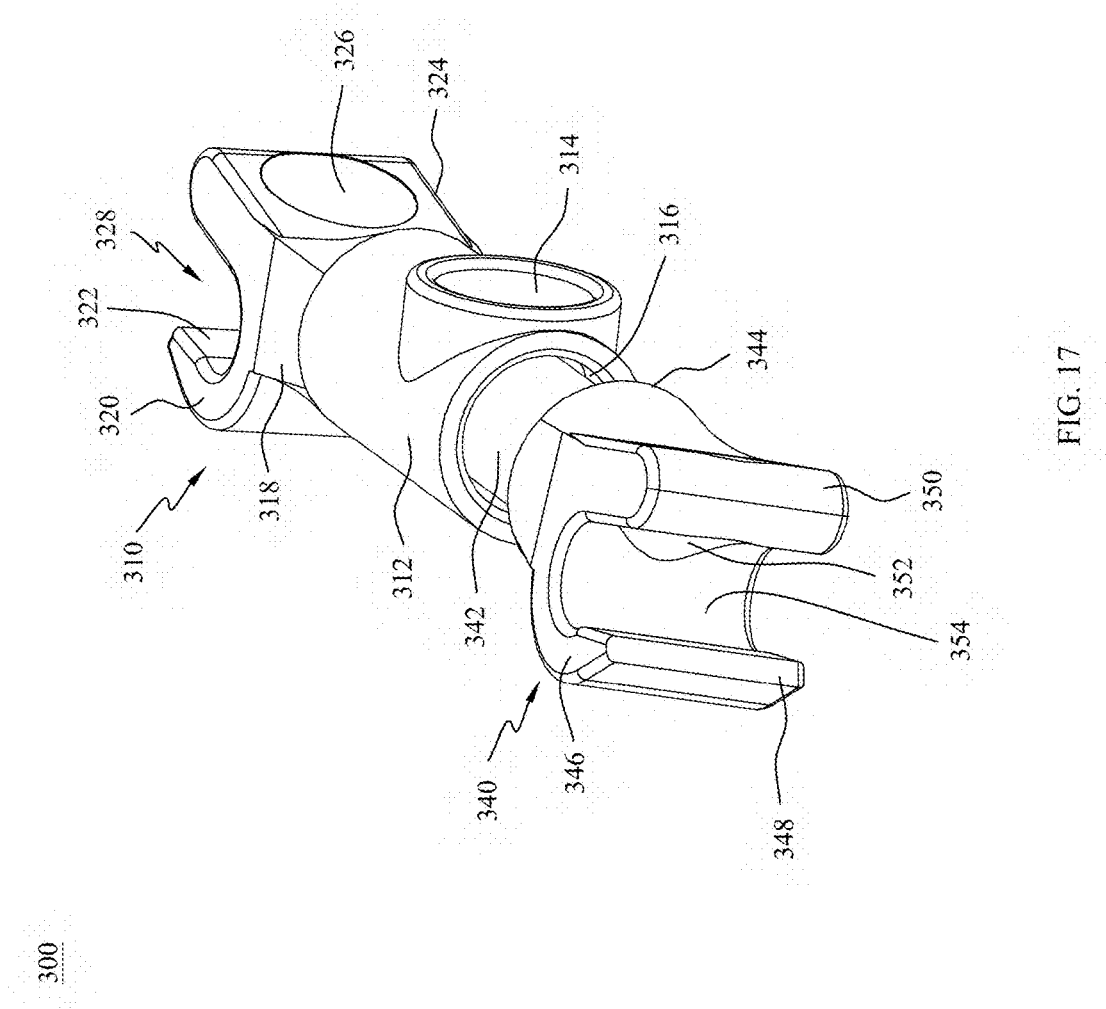
FIG. 17 is a first end view of the connector member of FIG. 13, in accordance with an aspect of the present invention.
Figure 18:
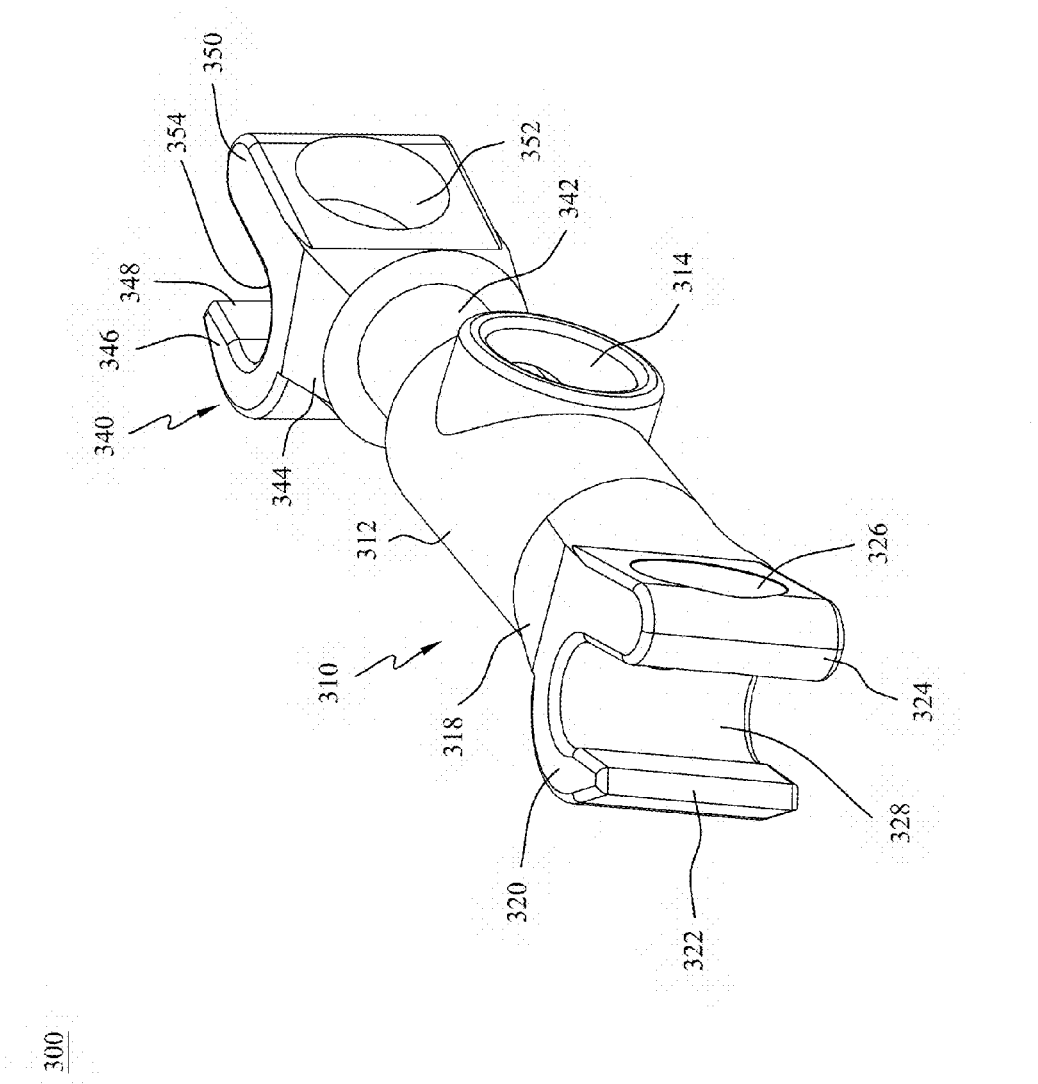
FIG. 18 is a second end view of the connector member of FIG. 13, in accordance with an aspect of the present invention.

As best illustrated in FIG. 9, the body 210 may also include a first hole 226 and a second hole 228 extending from the second end 218 into the channel 224. The first and second holes 226, 228 may be sized and shaped to receive a fastener, for example, a screw, set screw, or the like to secure the rib hook device 200 to the patient's ribs. The fastener (not shown) may be inserted into the first hole 226 and/or second hole 228 until it engages that patient's rib to secure the rib hook device 200 to the patient's rib.

Figure 23:
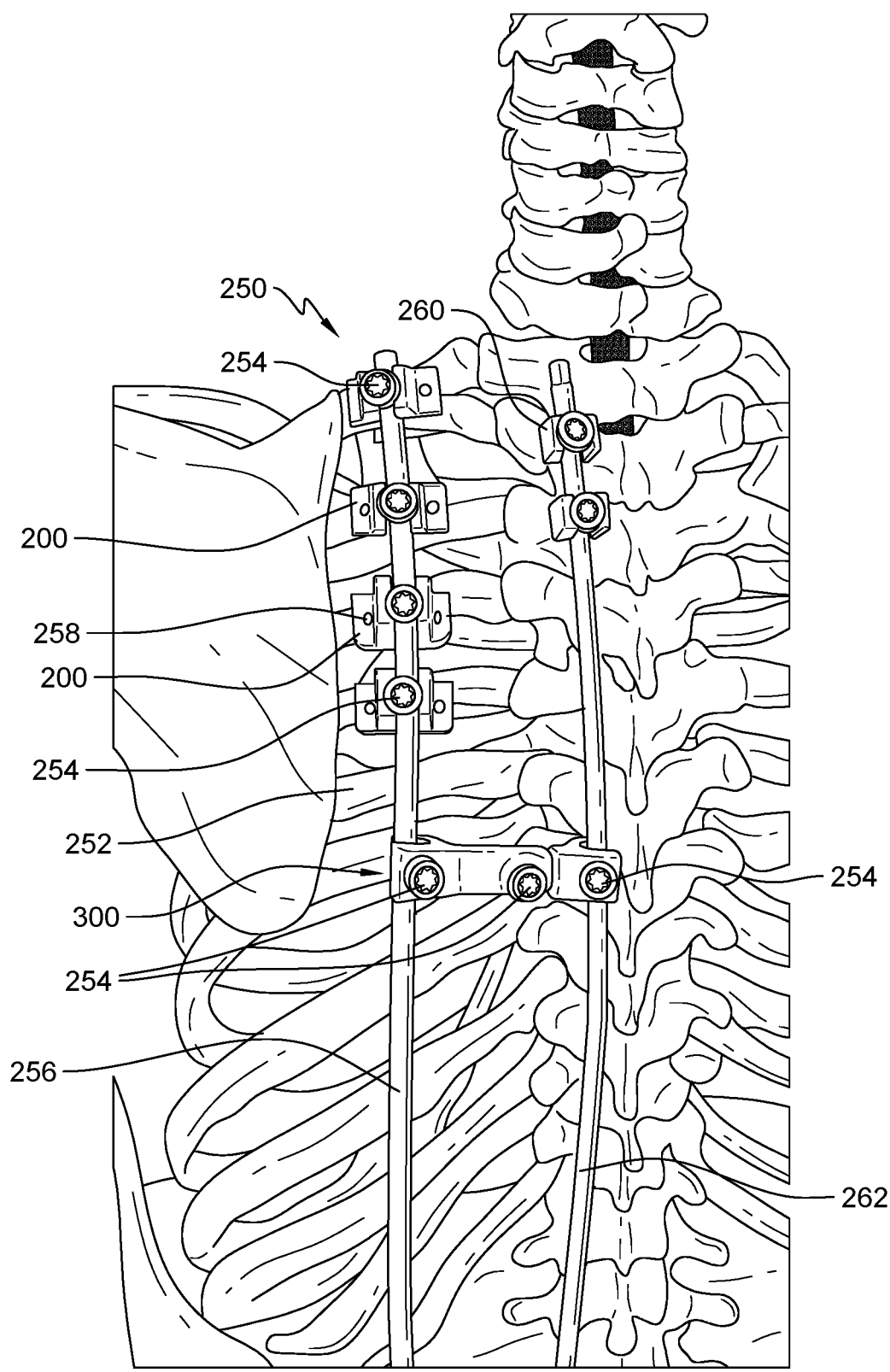
FIG. 23 is a posterior view of a plurality of rib hook devices of FIG. 7 on a patient's ribs, in accordance with an aspect of the present invention.

The rod attachment member 230 may extend out from the second end 218 of the body 210. With specific reference to FIG. 10, the rod attachment member 230 may extend away from the body 210 at an angle β. The angle β may be, for example, a cant angle that may be approximately 5° to 50°. The attachment member 230 may include a first arm 232 and a second arm 234. The first arm 232 and the second arm 234 may be spaced apart to form a groove 236 between the arms 232, 234. The groove 236 may be sized and shaped to receive a rod 256. The groove 236 may have, for example, an end that is shaped to match the shape of the rod 256, such as, a curved, arced, planar or angled shape. The first arm 232 may include, for example, a recess 238 on the inside of the first arm 232. The second arm 234 may include, for example, a recess 140 on the inside of the second arm 234. The recesses 238, 240 may be, for example, curved to receive fasteners 254, as shown in FIG. 23. The fasteners 254 may be, for example, screws, set screws, and the like to secure the rod 256 in the groove 236.

The rib hook device 200 may be, for example, an adult rib hook device sized to fit onto the ribs of an adult patient. Referring now to FIG. 23, a rib hook system 250 positioned on a patient's ribs 252 is shown. The rib hook system 250 may include a plurality of rib hook devices 200, a plurality of set screws 254, and a rod 256. At least one first rib hook device 200 of the plurality of rib hook devices 200 may be attached to a first rib 252 with the channel 224 open, for example, in a caudal direction. At least one second rib hook device 200 of the plurality of rib hook devices 200 may be attached to a second rib 252 with the channel 224 open, for example, in a cephalad direction. Although not shown, the at least one first rib hook device 200 and the at least one second rib hook device 200 may be positioned on the ribs in either a caudal or cephalad direction as desired by the surgeon to achieve the desired spinal correction. When the plurality of rib hook devices 200 are positioned on the patient's ribs, the attachment members 230 of each rib hook device 100 may extend out from the ribs in, for example, a generally posterior direction. The rod 256 may then be set into the groove 236 of each of the at least one first rib hook device 200 and the at least one second rib hook device 200 and secured to the rib hook devices 200 with fasteners 254, for example, set screws. The number of at least one first rib hook devices 200 and at least one second rib hook devices 200 may be selected based on the spinal deformity being corrected.

The rib hook system 250 may optionally include a second plurality of attachment devices 260 and a second rod 262. The second plurality of devices 260 may be, for example, a second set of rib hook devices 200 or pedicle screw devices 260. The second plurality of devices 260 and second rod 258 may be positioned, for example, spaced apart from the first plurality of rib hook devices 200 and rod 256. If a second set of rib hook devices 200 are used, then the second set of rib hook devices 200 may be positioned on and secured to the patient's ribs, as described in greater detail above and which will not be described again here for brevity sake. If pedicle screw devices 260 are used, then the pedicle screw devices 260 may be secured to the patient's spine using a method known to one skilled in the art. In FIG. 23 the second plurality of devices 260 are pedicle screw devices 260 which are secured to the patient's spine.

Referring now to FIGS. 13-21 and 23, a connector member 300 is shown. The connector member 300 may include a first member 310 and a second member 340. The first member 310 may be, for example, a female member. The first member 310 may include a first coupling portion 312 with a securement opening 314 and an opening 316. The opening 316 may extend along the longitudinal axis of the first member 310 and be sized to receive the second member 340. The opening 316 may extend into the first coupling portion 312 from a first end. The securement opening 314 may extend from an exterior surface on a side of the first coupling portion 312 into the opening 316. The securement opening 314 may extend perpendicular to the opening 316. The securement opening 314 may be sized and shaped to receive a fastener 254, for example, a screw, set screw, or the like to secure the second member 340 to the first member 310, as shown in FIG. 23. The first and second members 310, 340 may be adjustable to select the desired length of the connector member 300 based on the distance between the two rods 256, 262. The adjustable length may be, for example, in the coronal plane. The first and second members 310, 340 may be telescoping to allow for the second member 340 to slide with respect to the first member 310 and vice versa. In addition, the first and second members 310, 340 may rotate relative to each other to allow for the first member 310 to couple to the rod 256 at a first angle and the second member 340 to couple to the rod 262 at a second angle with respect to each other. The fastener 254 may be loosened to lengthen or shorten the length of the connector member 300. Once the desired length of the connector member 300 is obtained the fastener (not shown) may be tightened to secure the second member 340 to the first member 310.

The first member 310 may also include a neck 318 extending out from an end of the first member 310 opposite the opening 316. A first arm 320 may extend out from the neck 318 in a first direction and a second arm 324 may extend out from the neck 318 in a second direction. The first and second directions may be opposite each other. The first arm 320 may be, for example, curved as it extends away from the neck 318. The first arm 320 may include, for example, an angled or tapered portion 322 at the end opposite the neck 318. The first arm 320 may be shaped, for example, to extend around and secure to the proximal side of a rod. The second arm 324 may extend away from the neck 318 at an angle. The second arm 324 may include a fastener opening 326 for receiving a fastener 254, for example, a screw, set screw or the like to secure the connector member 300 to a rod 256, as shown in FIG. 23. The neck 318 may be tapered as it extends from the first and second arms 320, 324 to the first coupling portion 312. The first arm 320 and the second arm 324 may be positioned to form a channel 328. The channel 328 may be, for example, sized to receive the rod 256, as shown in FIG. 23. The bottom or base of the channel 328 may also be, for example, shaped to correspond to the shape of the rod (not shown). For example, the bottom or base of the channel 328 may be curved, arced, planar or angled to securely receive the rod 256.

Figure 19:
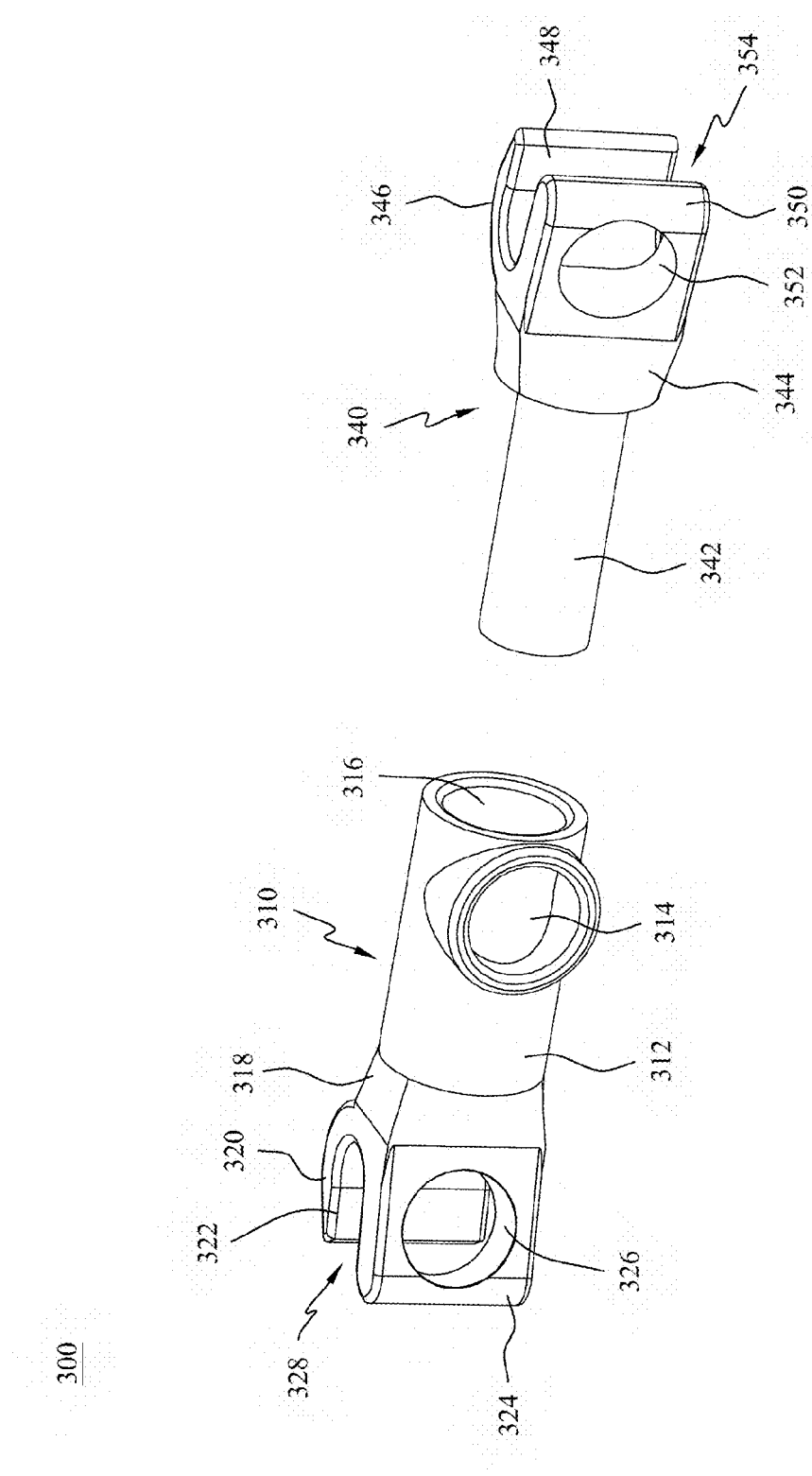
FIG. 19 is an exploded, side perspective view of the connector member of FIG. 13, in accordance with an aspect of the present invention.
Figure 20:
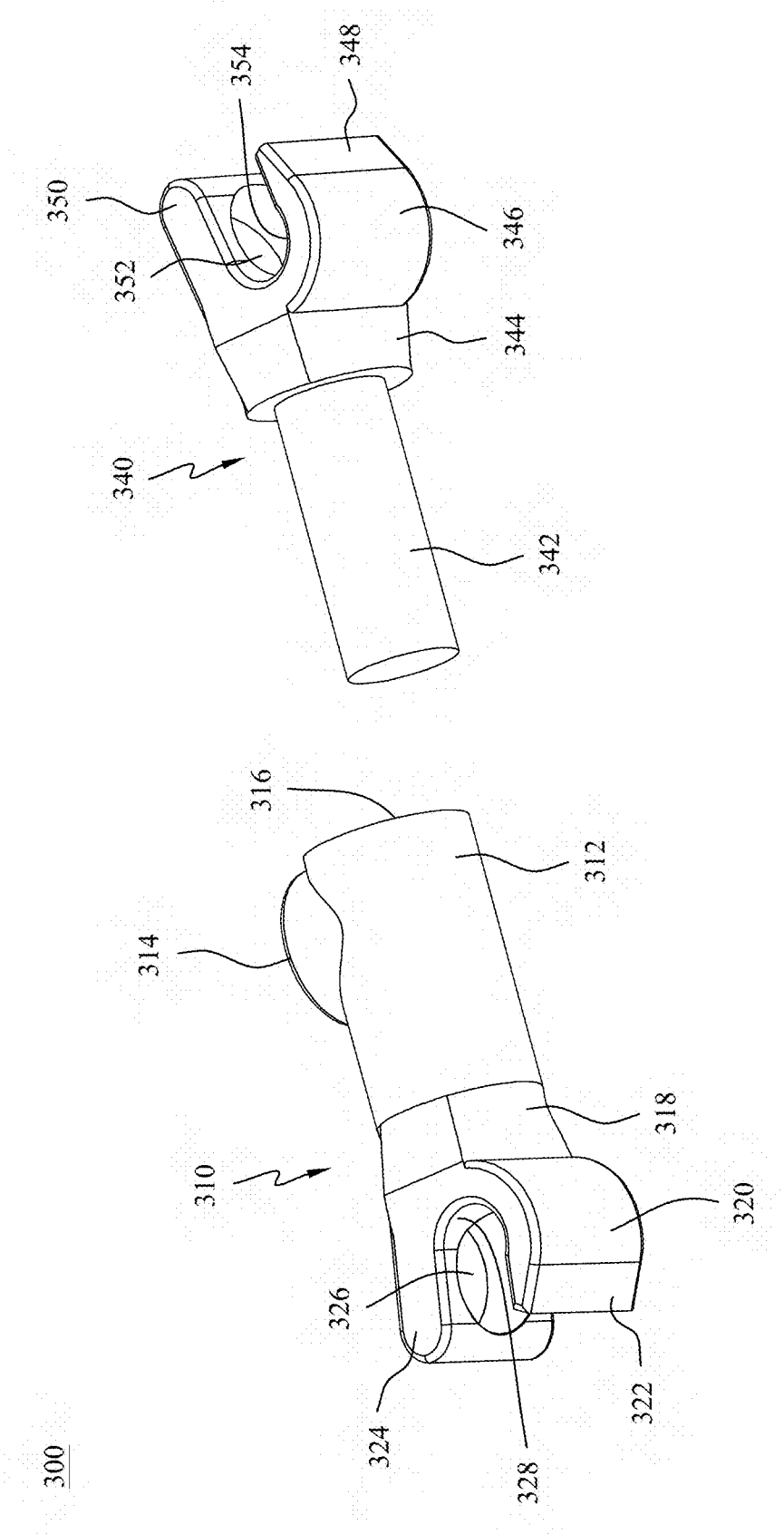
FIG. 20 is another exploded, side perspective view of the connector member of FIG. 13, in accordance with an aspect of the present invention.
Figure 21:
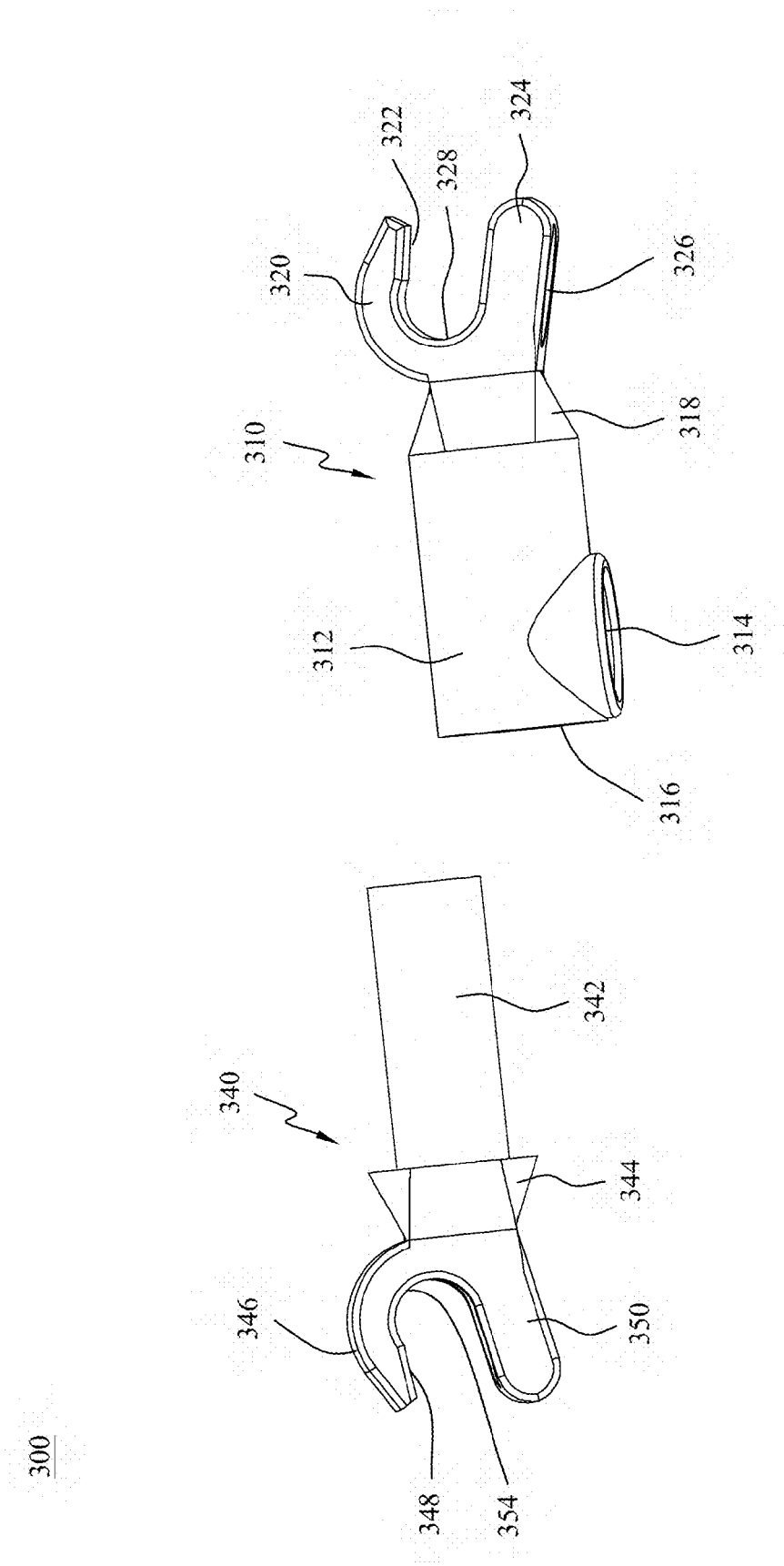
FIG. 21 is an exploded, top perspective view of the connector member of FIG. 13, in accordance with an aspect of the present invention.

The second member 340, may be, for example, a male member. The second member 340 may include a rod 342, a neck 344, a first arm 346, and a second arm 350. The neck 344 may extend between the rod 342 and the first and second arms 346, 350. The neck 344 may be tapered as it extends from the first and second arms 346, 350 to the rod 342. The rod 342 may be sized and shaped to correspond to and be received within the opening 316. As shown in FIG. 19, the rod 342 and opening 316 may be, for example, cylindrical, circular, round or the like. Alternative corresponding shapes for the rod 342 and opening 316 are also contemplated, such as, another rounded shape or any polygonal shape. The first arm 346 may extend out from the neck 318 in a first direction and the second arm 350 may extend out from the neck 318 in a second direction. The first arm 346 may be, for example, curved as it extends away from the neck 318. The first arm 346 may also include, for example, an angled or tapered portion 348 at the end opposite the neck 318. The first arm 346 may be shaped, for example, to extend around and secure to the proximal side of a rod. The second arm 350 may extend away from the neck 318 at an angle. The second arm may also include a fastener opening 352 for receiving a fastener 254, for example, a screw, set screw, or the like to secure the connector member 300 to a rod 262. The first arm 346 and second arm 350 may be positioned to form a channel 354. The channel 354 may be, for example, sized to receive the rod 262, as shown in FIG. 23. The bottom or base of the channel 354 may also be, for example, shaped to correspond to the shape of the rod (not shown). For example, the bottom or base of the channel 354 may be curved, arced, planar or angled to securely receive the rod 262.

As shown in FIG. 23, the rib hook system 250 may also include at least one connector member 300. The connector member 300 may be used to couple the first and second rods 256, 262 and provide additional support to the rib hook system 250.

A method of using the rib hook devices 100, 200 may include preparing the patient for surgery by exposing at least a portion of the patient's ribs. The method may also include coupling at least one first rib hook device 100, 200 to a first rib 152 and at least one second rib hook device 100, 200 to a second rib 152. The at least one first rib hook device 100, 200 may be, for example, positioned so the channel 124, 224 is open in a first direction. The at least one second rib hook device 100, 200 may be, for example, positioned so the channel 124, 224 is open in a second direction. In one embodiment, the first direction may be, for example, a caudal direction and the second direction may be, for example, a cephalad direction. In another embodiment, the first direction may be, for example, a cephalad direction and the second direction may be, for example, a caudal direction. In other embodiments, the first and second direction may be selected from either a caudal or cephalad direction depending on the desired correction. Once the rib hook devices 100, 200 are positioned onto the patient's ribs, the rib hook devices 100, 200 may optionally be secured to the patient's ribs. If the rib hook devices 100, 200 are secured, the devices 100, 200 may be secured using, for example, at least one fastener 258, as shown in FIG. 23. The at least one fastener 258 may be, for example, a screw, set screw, or the like to be inserted through the body 110, 210 of the rib hook device 100, 200 and engage the patient's rib 152, 252. After the rib hook devices 100, 200 are positioned on or secured to the patient's ribs 152, 252, a rod 156, 256 may be inserted into the groove 136, 236 of the rod attachment member 130, 230. The rod 156, 256 may be positioned along the rib hook devices 100, 200 at the locations for the desired correction and secured using fasteners 154, 254.

In one embodiment of the method, a second set of rib hook devices 100, 200 may be positioned on or secured to a patient's ribs 152, 252 or a set of pedicle screws 260 may be secured to a patient's spine. The second set of rib hook devices 100, 200 may be positioned on or secured to the patient's ribs 152, 252 as described in greater detail above with reference to the first set of rib hook devices 100, 200. If pedicle screws 260 are used they may be secured to the patient's spine with any known technique. After the second set of rib hook devices 100, 200 or pedicle screws 260 are secured, a rod 262 may be inserted and coupled to the second set of rib hook devices 100, 200 or pedicle screws 260 using fasteners, such as, screws, set screws or the like to secure the rod 262 to the second set of rib hook devices 100, 200 or pedicle screws 260. At least one connector member 300 may then be positioned between the first rod 156, 256 and the second rod 262, as shown in FIG. 23. The rod 256 may be inserted into the channel 328 of the first member 310 of the connector member 300 and secured in the desired position using a fastener 254. Next, the rod 342 of the second member 340, if not already coupled to the first member 310, may be inserted into the opening 316 of the first member 310. The channel 354 of the second member 340 may then be positioned to receive the second rod 262. Once the rod 262 is in the desired position within the channel 354, a fastener 254 may be inserted into the fastener opening 352 to secure the rod 262 to the second member 340. Then, the length of the connector member 300 and orientation between the first and second members 310, 340 may be set for the desired correction.

After the desired rib hook devices 100, 200 and rods 156, 256, 262 have been positioned and secured to the patient's ribs, the patient's incisions may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A rib hook device, comprising:
   a body comprising:
     a first side;
     a second side;
     a first end extending between the first side and the second side; and
     a second end extending between the first side and the second side and positioned opposite the first end;
     wherein the first end is curved between a top side and a bottom side as the first end extends between the first side and the second side forming a concave surface on the first end of the body; and
   a rod attachment member coupled to and extending away from the second end of the body.

2. The rib hook device of claim 1, wherein the body further comprises:
   a channel extending into the body from the bottom side toward the top side.

3. The rib hook device of claim 2, wherein the channel has a radius in the sagittal plane when implanted in a patient.

4. The rib hook device of claim 2, wherein the body has a curvature in the transverse plane when implanted in a patient.

5. The rib hook device of claim 2, wherein the body further comprises:
   at least one hole extending from the second end through the body and into the channel, wherein the at least one hole is positioned adjacent to an exterior surface of the rod attachment member and between the exterior surface of at least one of a first arm and a first end and a second arm and a second end.

6. The rib hook device of claim 2, wherein the body further comprises:
   a first interior surface opposite the first end on a first side of the channel;
   a second interior surface opposite the second end on a second side of the channel; and
   wherein the first interior surface and the second interior surface curve as the first interior surface and the second interior surface extend between the first side and the second side.

7. The rib hook device of claim 1, wherein the rod attachment member extends from the top side of the body at an angle greater than 180°.

8. The rib hook device of claim 7, wherein the angle is a cant angle.

9. The rib hook device of claim 1, wherein the rod attachment member comprises:
   a first arm;
   a second arm spaced apart from the first arm; and
   a groove positioned between the first arm and the second arm.

10. The rib hook device of claim 9, wherein the first arm comprises:
    a first recess positioned on an inside of the first arm; and
    wherein the second arm comprises:
      a second recess positioned on an inside of the second arm.

11. A rib hook system, comprising:
    at least one rib hook device, wherein the at least one rib hook device, comprises:
      a body comprising:
        a first side;
        a second side;
        a first end extending between the first side and the second side; and
        a second end extending between the first side and the second side and positioned opposite the first end;
        wherein the first end is curved between a top side and a bottom side as the first end extends between the first side and the second side forming a concave surface on the first end of the body; and
      a rod attachment member coupled to and extending away from the second end of the body;
    a first rod for engaging the rod attachment member of the at least one rib hook device; and
    at least one fastener for securing the first rod to the at least one rib hook device.

12. The rib hook system of claim 11, wherein the at least one rib hook device comprises:
    a channel extending into the body from the bottom side toward the top side and across the body from the first side to the second side.

13. The rib hook system of claim 12, wherein the channel has a radius in the sagittal plane and wherein the body has a curvature in the transverse plane.

14. The rib hook system of claim 12, wherein the rod attachment member comprises:
    a first arm;
    a second arm spaced apart from the first arm;
    a groove positioned between the first arm and the second arm; and
    wherein the first arm and the second arm extend away from the body at an angle.

15. The rib hook system of claim 11, further comprising:
    a connector member; and
    a second rod.

16. The rib hook system of claim 15, wherein the connector member comprises:
    a first member;
    a second member sized to engage the first member; and
    at least one fastener to couple the first member to the second member.

17. The rib hook system of claim 16, wherein the first member comprises:
    a first coupling portion with an opening at a first end and extending along a longitudinal axis of the first coupling portion;
    a neck extending out from an end of the first coupling portion opposite the opening;
    a first arm extending in a first direction from the neck; and a second arm extending in a second direction from the neck, the second direction being opposite the first direction;
wherein the first arm and the second arm form a channel.

18. The rib hook system of claim 17, wherein the second member comprises:
a rod with a first end and a second end;
a neck extending out from the second end;
a first arm extending in a first direction from the neck; and
a second arm extending in a second direction from the neck, the second direction being opposite the first direction;
wherein the first arm and the second arm form a channel.

19. The rib hook system of claim 18, wherein the first coupling portion of the first member, further comprises:
a securement opening extending from an exterior surface into the opening, wherein the securement opening receives the at least one fastener.

20. A method of using a rib hook system, comprising:
obtaining a rib hook system, the rib hook system comprising:
at least two rib hook devices, wherein each rib hook device, comprises:
a body comprising:
a first side;
a second side;
a first end extending between the first side and the second side; and
a second end extending between the first side and the second side and positioned opposite the first end;
wherein the first end is curved between a top side and a bottom side as the first end extends between the first side and the second side forming a concave surface on the first end of the body; and
a rod attachment member coupled to and extending away from the second end of the body;
a first rod; and
at least one fastener;
exposing at least a portion of a patient's ribs;
coupling a first rib hook device of the at least two rib hook devices to a first rib;
coupling a second rib hook device of the at least two rib hook devices to a second rib;
inserting the first rod to engage the first rib hook device and the second rib hook device;
securing the first rod to the first rib hook device and the second rib hook device; and
closing the patient.

* * * * *